US 6,699,190 B2

(12) United States Patent
Mesaros et al.

(10) Patent No.: US 6,699,190 B2
(45) Date of Patent: Mar. 2, 2004

(54) DIAGNOSTIC ULTRASOUND SYSTEM CART WITH INTEGRAL WRIST PAD

(75) Inventors: Robert Mesaros, Bothell, WA (US); Yas Matsui, Redmond, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/155,504

(22) Filed: May 23, 2002

(65) Prior Publication Data

US 2003/0220566 A1 Nov. 27, 2003

(51) Int. Cl.[7] .............................. A61B 8/00; B68G 5/00
(52) U.S. Cl. ...................... 600/437; 248/118; 248/918
(58) Field of Search .............................. D24/186, 160, D24/100; 400/472, 691, 715; 248/118, 918; 600/437, 443, 442

(56) References Cited

U.S. PATENT DOCUMENTS

| | | | |
|---|---|---|---|
| 4,870,954 A | 10/1989 | Satoh | |
| 5,205,175 A | 4/1993 | Garza et al. | |
| 5,251,631 A | 10/1993 | Tsuchiko et al. | |
| 5,315,999 A | * 5/1994 | Kinicki et al. | 600/443 |
| D368,521 S | * 4/1996 | Asai et al. | D24/160 |
| 5,570,268 A | * 10/1996 | Selker | 361/683 |
| D379,231 S | * 5/1997 | Ungari | D24/160 |
| 5,927,662 A | * 7/1999 | West et al. | 248/118 |
| 5,938,352 A | * 8/1999 | Chen | 400/472 |
| 5,980,143 A | 11/1999 | Bayer et al. | |
| 6,142,940 A | * 11/2000 | Lathbury et al. | 600/437 |
| 6,312,381 B1 | 11/2001 | Knell et al. | |
| 6,361,497 B1 | * 3/2002 | Lathbury et al. | 600/437 |

\* cited by examiner

*Primary Examiner*—Francis J. Jaworski
(74) *Attorney, Agent, or Firm*—W. Brinton Yorks, Jr.

(57) ABSTRACT

A control panel for a diagnostic ultrasound system includes a keyboard with a wrist pad that stows beneath the control panel, and extends from the control panel when needed. The keyboard wrist pad integrates smoothly into the front of the control panel when the keyboard is in the stowed position. The keyboard wrist pad can also be integrated into the top surface of the edge of the control panel and can serve as a wrist pad for either the control panel or the keyboard when the keyboard is extended.

19 Claims, 12 Drawing Sheets

DIAGNOSTIC ULTRASOUND SYSTEM CART WITH INTEGRAL WRIST PAD

This invention relates to ultrasonic diagnostic imaging systems and, in particular, to ultrasound systems with integral wrist support pads.

Cart-borne ultrasound systems should be compact and easy to roll to a diagnostic lab or patient bedside. In use, these systems should be comfortable and convenient for the clinician to operate. Typically, such ultrasound systems have a control panel by which the clinician adjusts the features and performance of the system. These systems also generally have a keyboard by which the clinician can type in patient information and notations on images and reports produced by the system. In the past the keyboard has generally been made a part of the control panel, thereby presenting the full range of controls including the keyboard immediately in front of the operator. For a more compact design, it is desirable to integrate the control panel and keyboard together. For instance, if the keyboard is mounted beneath the control panel on a sliding drawer, the drawer and keyboard can be pulled out from under the control panel when needed, and rolled back under the control panel when not in use. Such an arrangement allows the control panel to be made smaller and more compact, as the keyboard is not a part of the control panel surface.

The clinician can spend many hours during the day operating the ultrasound system. To guard against fatigue and repetitive stress injuries and to afford comfort to the user, it is desirable to provide a support for the clinician's hand or arm while operating the ultrasound system. Such a support should be convenient to use as well as providing the necessary support, and should not detract from a clean and elegant system design.

In accordance with the principles of the present invention, an ultrasound system control panel has the keyboard integrated into the control panel structure. The keyboard slides out from beneath the control panel for use, and slides back under the control panel when not needed. The control panel has a wrist pad to support the operator's hand when operating the control panel. The keyboard is integrated into this wrist pad and has its own wrist pad when extended for use. Alternatively, the keyboard wrist pad can serve both the keyboard and the control panel. When the keyboard and its wrist pad are partially extended, the keyboard wrist pad provides an adjustable wrist pad for larger hands.

Figure 1:
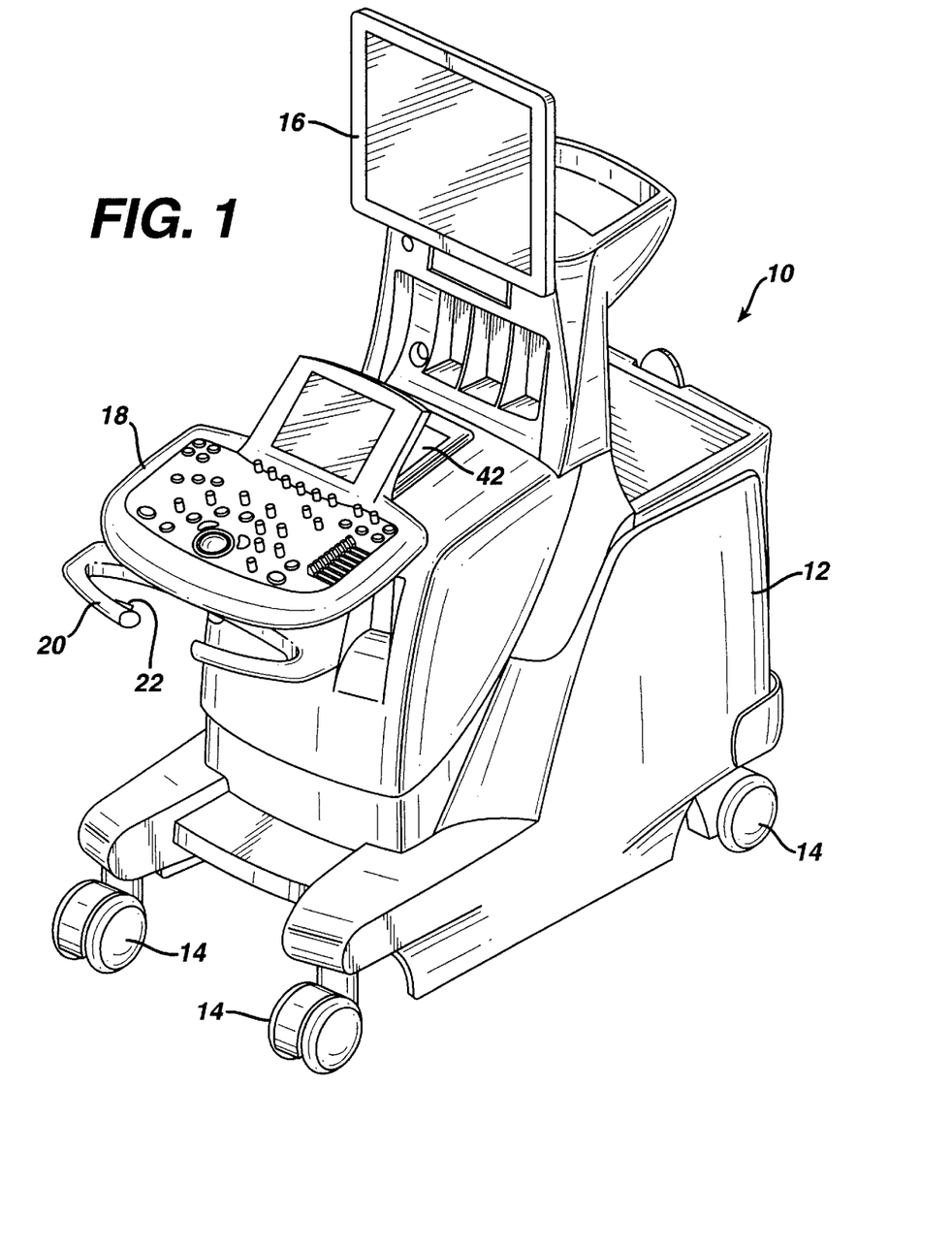
FIG. 1 illustrates a cart-borne ultrasound system in perspective.

Referring first to FIG. 1, a cart-borne ultrasound system 10 is shown in perspective. The cart includes an electronics bay 12 inside of which are located printed circuit boards for electronically processing received ultrasound signals. The ultrasound signals are processed to produce an image which is displayed on a display 16. The cart is mounted on wheels or casters 14 so that it can be rolled to a lab or a patient's bedside. In the front of the cart is a control panel 18, which contains a number of knobs, buttons, slide switches, and a trackball by which a user controls the operation of the ultrasound system. The control panel is mounted above a handle 20 which extends from the front of the ultrasound system. The handle 20 can be used to pull the cart to move it from one location to another. On the inside of the handle 20 is a lift release button 22 which unlocks a lift mechanism 42 for the control panel, enabling the control panel to be raised or lowered to an elevation which is comfortable for the user. The lift mechanism is more fully described in concurrently filed U.S. patent application Ser. No. 10/154,733, the subject matter of which is incorporated herein by reference.

Figure 2:
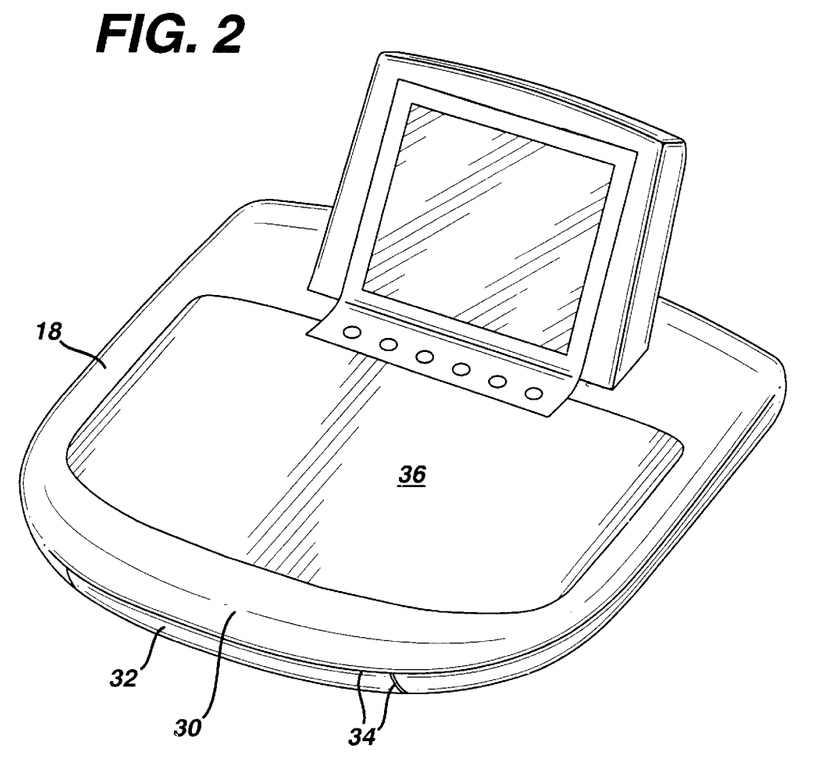
FIGS. 2 through 6a illustrate a first embodiment of the present invention in which a keyboard is integrated into the wrist pad of an ultrasound system control panel.

FIG. 2 illustrates an ultrasound system control panel constructed in accordance with the principles of a first embodiment of the present invention. Located in the front of the control panel 18, and preferably extending around the periphery of the control panel, is a wrist pad 30. The wrist pad 30 supports the base of the palm or wrist of the user's hand when operating the controls located on the control area 36 of the control panel 18. The wrist pad wraps over the front of the control panel, in which there is a recess 34. Located in the recess 34 is a keyboard for the ultrasound system with its own wrist pad 32. As FIG. 2 illustrates, the wrist pad 32 for the keyboard is smoothly integrated into the front of the control panel wrist pad 30, providing a clean and compact design appearance when the keyboard is stored under the control panel.

Figure 2A:
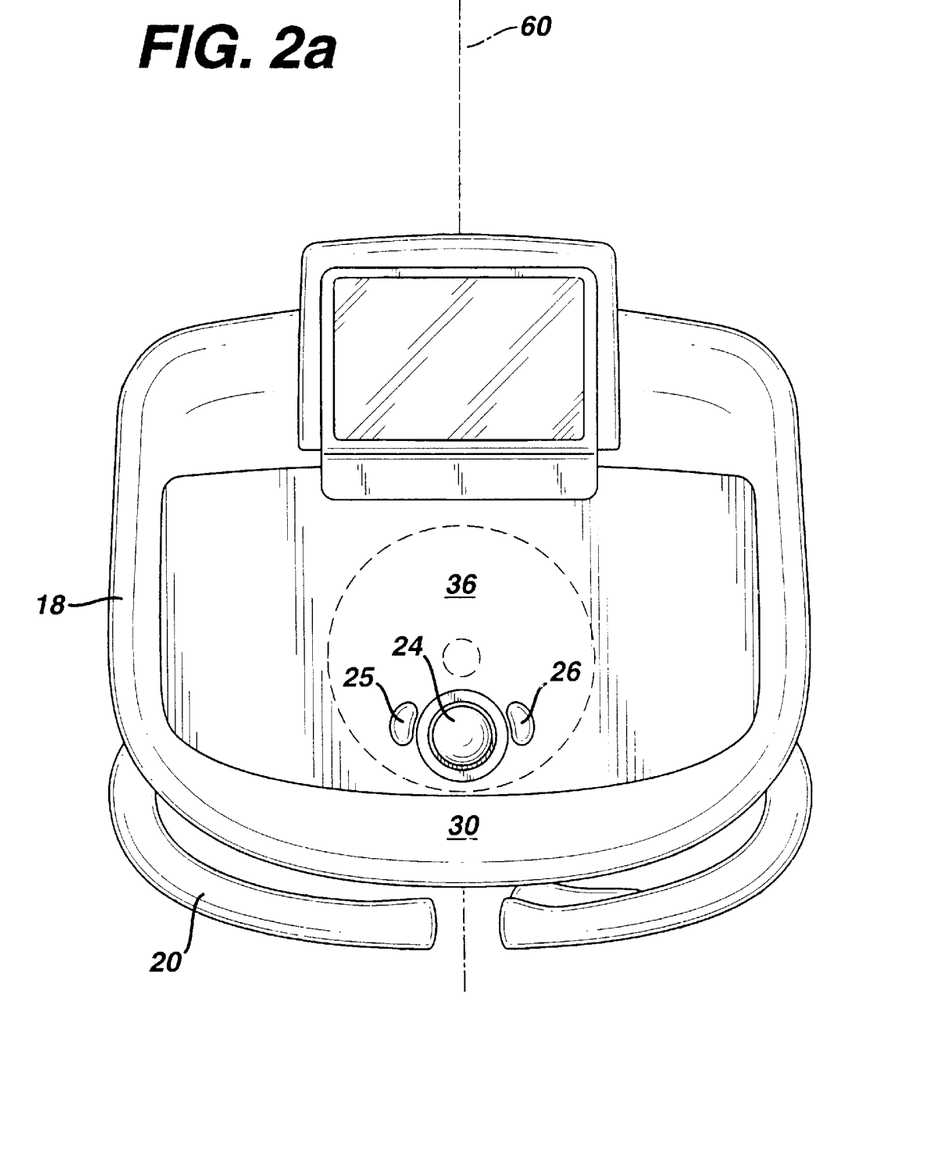

FIG. 2a is a plan view of the control panel 18 of FIG. 2, which also shows the handle 20. In a preferred embodiment the control panel can articulate laterally to conform to the location of the user at one side of the ultrasound system cart or the other, as described more fully in concurrently filed U.S. patent application Ser. No. 10,155,459. When the control panel is in its nominal center position it is centered about the center line 60 of the ultrasound system as shown in FIG. 1. FIG. 2a also shows the location of a trackball 24 on the control panel 18 just in front of the wrist pad 30. As is evident from the drawing, the user can rest his or her wrist on the wrist pad 30 while manipulating the trackball 24 or control buttons 25,26 located around the trackball.

Figure 3:
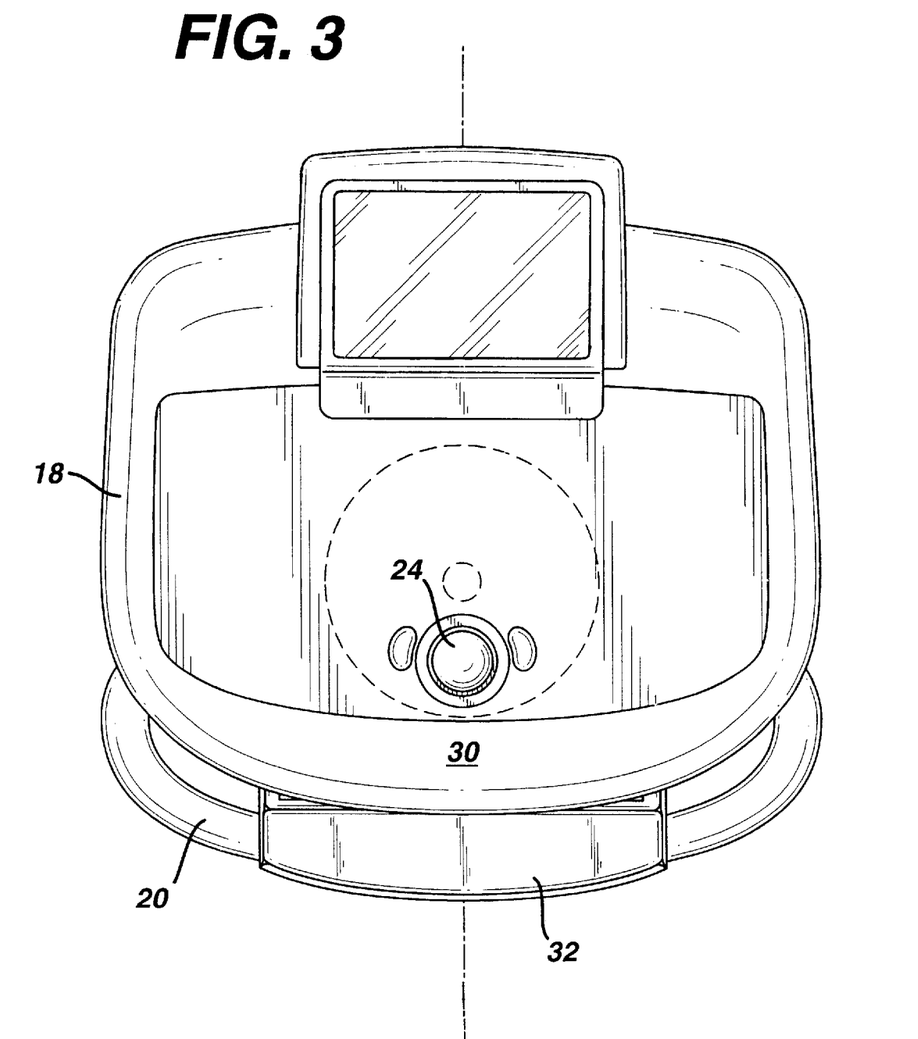
Figure 4:
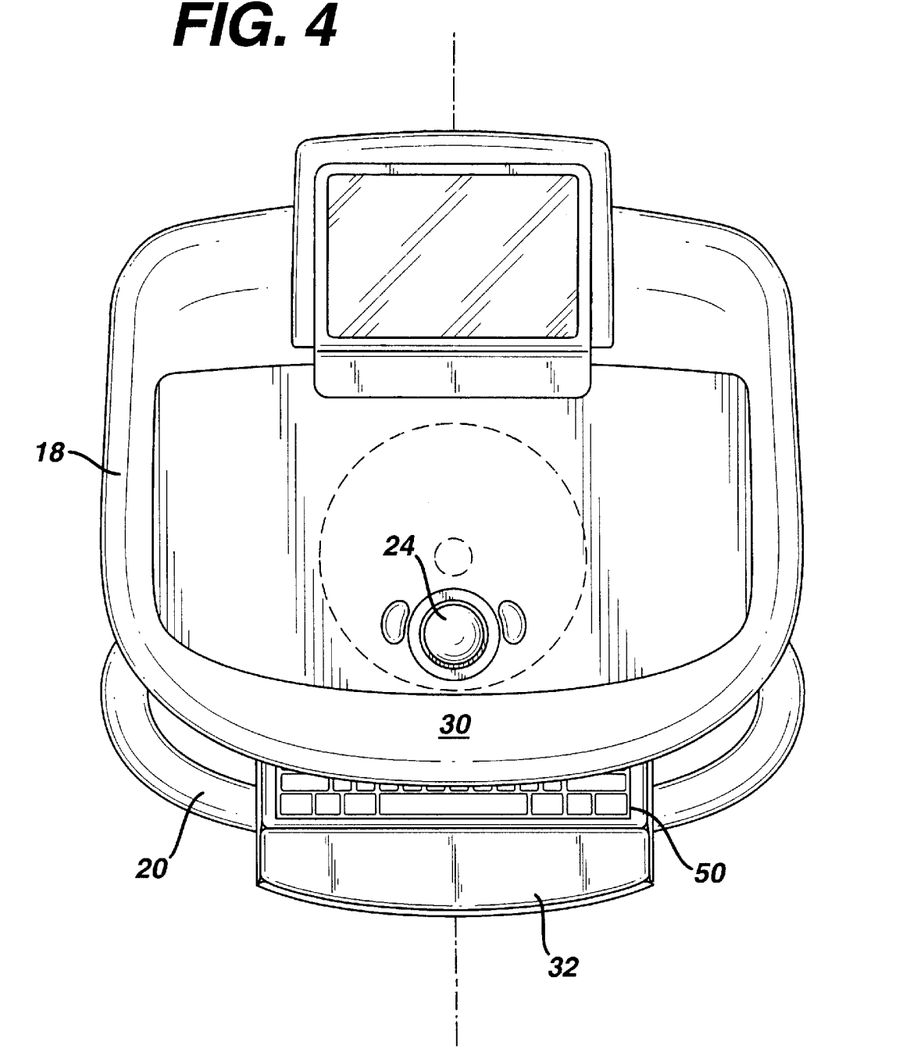
Figure 5:
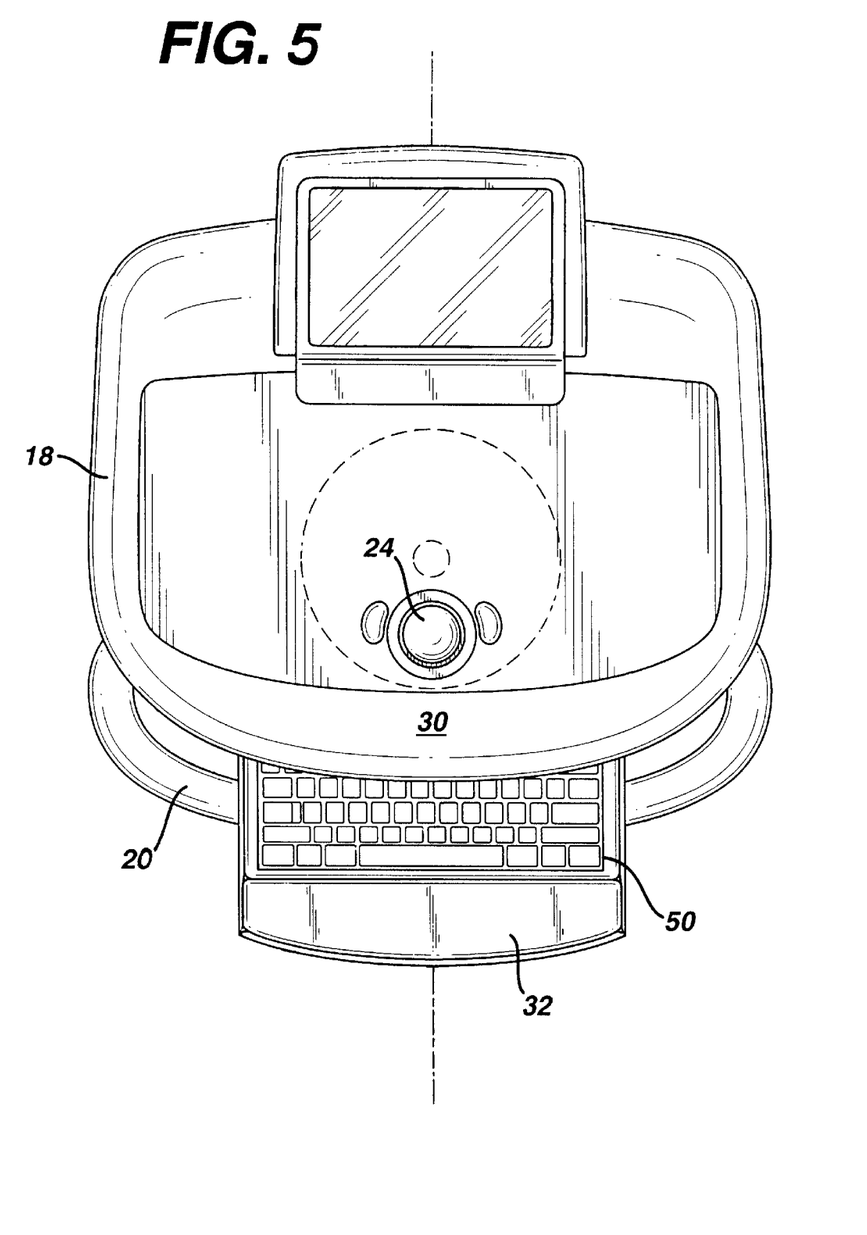
Figure 6:
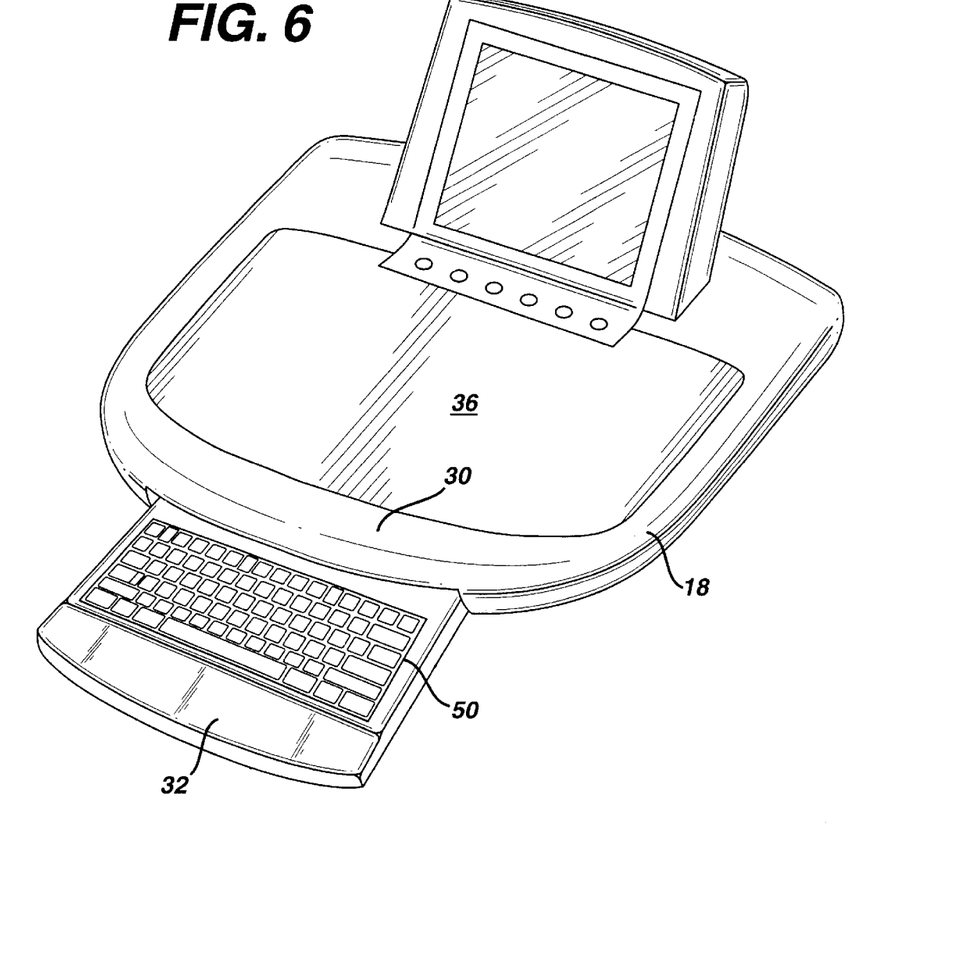
Figure 6A:
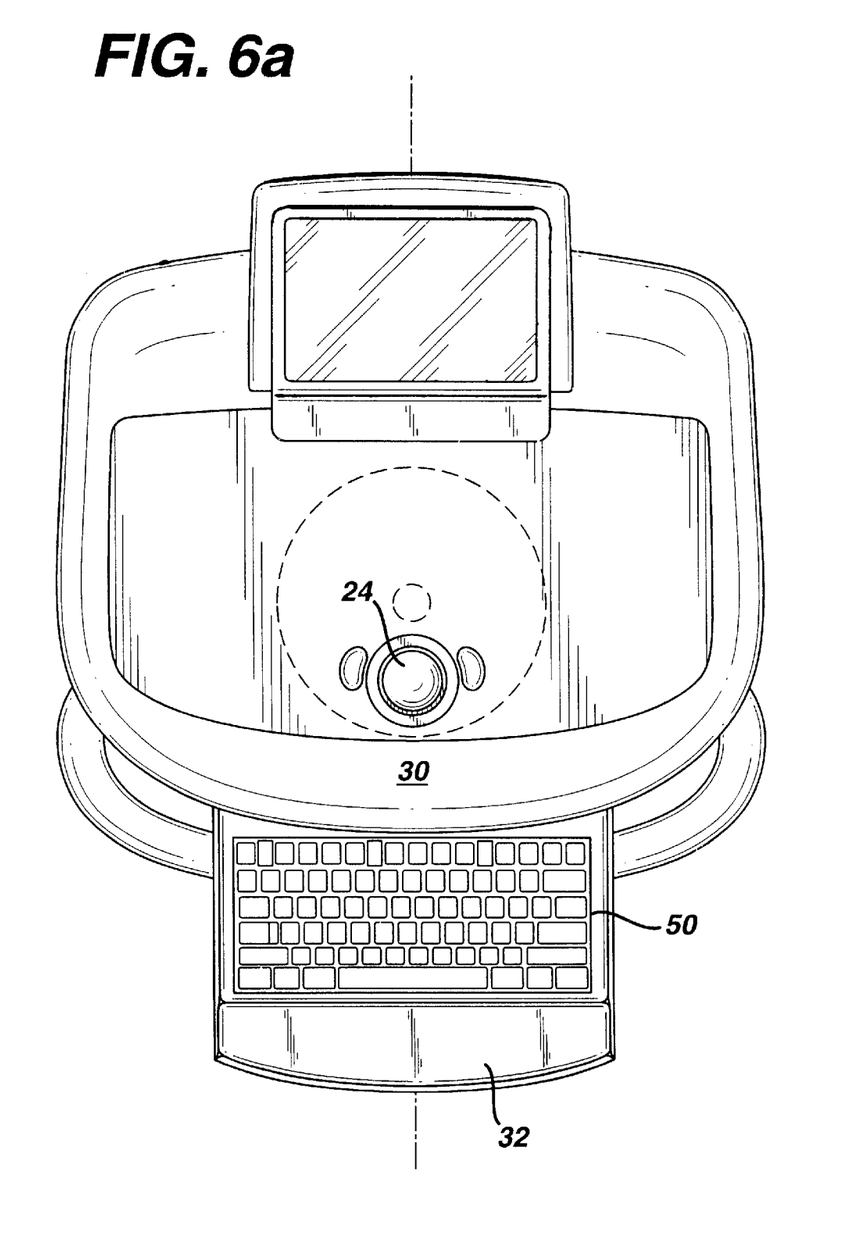

FIG. 3 shows the control panel 18 and handle 20 with the keyboard withdrawn a small distance from its stored location under the control panel. The wrist pad 32 of the keyboard is seen extending in front of the control panel. In FIG. 4 the keyboard 50 is extended further from the recess in the control panel wrist pad and is partially visible. In FIG. 5 the keyboard 50 is extended even further from the recess 34, and in FIGS. 6 and 6a the keyboard 50 is shown fully extended from the control panel. As these latter drawings illustrate, the keyboard may be operated while the user's wrists are supported on the keyboard wrist pad 32, and the trackball 24 and controls of the control panel can be operated with the user's wrist supported on the control panel wrist pad 30. When the user is finished using the keyboard 50, it can be stowed back in the recess 34 as the user continues to operate the controls on the control panel with a wrist or hand supported on the wrist pad 30.

Figure 7:
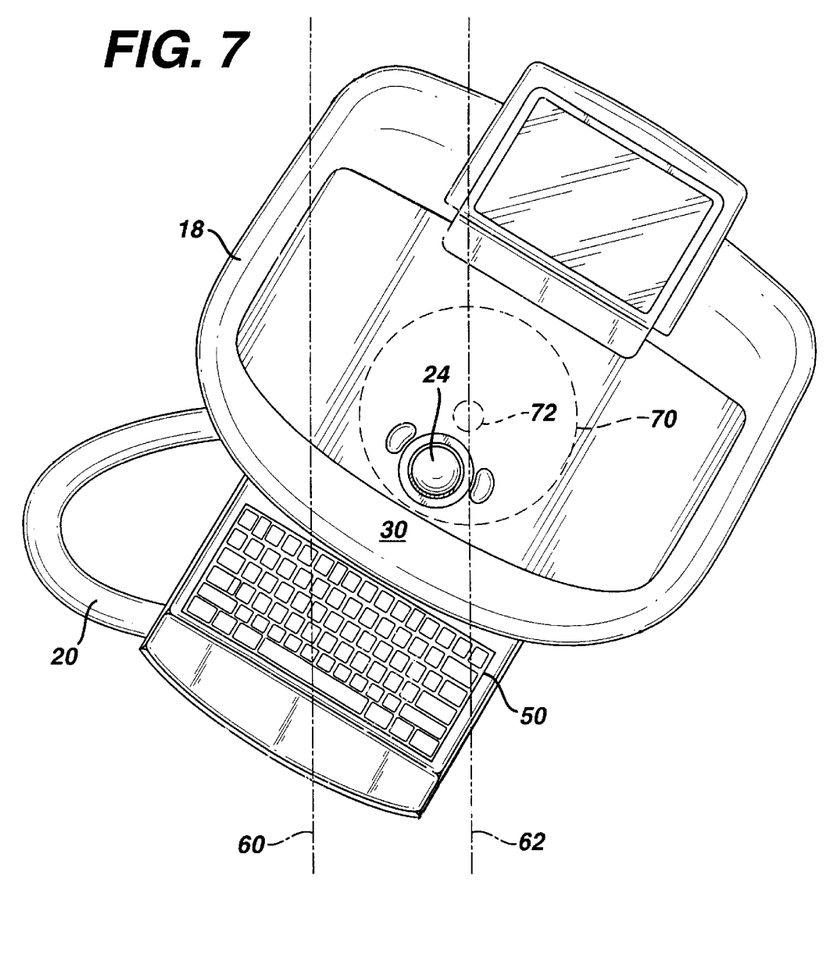
FIGS. 7 through 10 illustrate a second embodiment of the present invention in which a keyboard is integrated into the wrist pad of the control panel and has a wrist pad which may be used for either the control panel or the keyboard.

FIG. 7 shows the control panel 18 with keyboard 50 extended when the control panel has been moved laterally to one side of the cart. This drawing and previous drawings show a swivel plate 70 in phantom which pivots about a pivot point 72. The control panel and keyboard are mounted for lateral articulation on a track (not shown) which allows the control panel and keyboard to be moved laterally to be centered about dashed line 62 as opposed to the nominal center line 60. At any point in its lateral path of travel the control panel and keyboard can be swiveled by means of the swivel plate 70 on which the control panel is mounted. This lateral articulation and swiveling of the control panel is more fully described in concurrently filed U.S. patent application Ser. No. 10/155,459 which is incorporated herein by reference. This combination of raising and lowering, lateral articulation and swiveling permit the control panel and keyboard with their wrist pads to be located in a position most comfortable for a wide variety of users.

Figure 8:
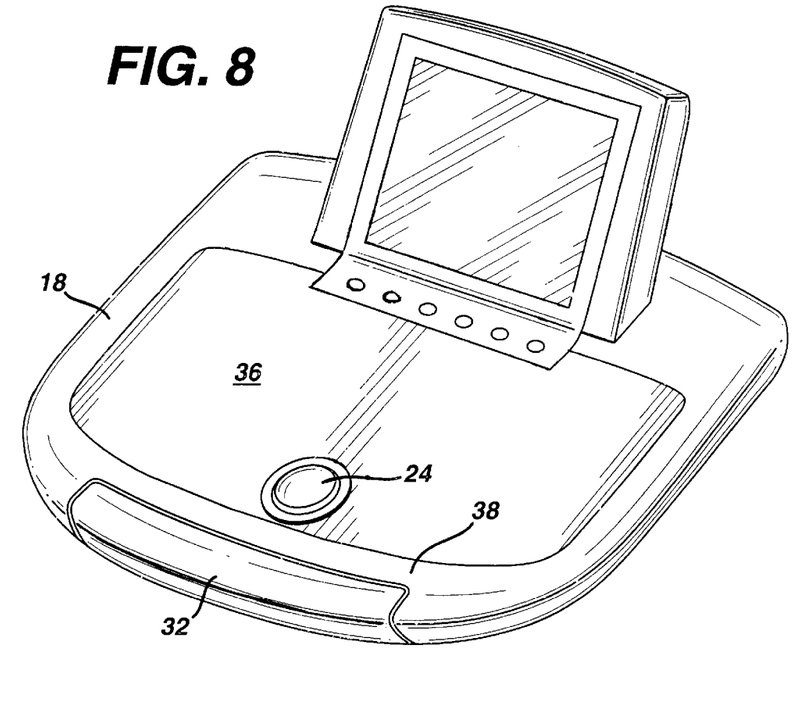
Figure 8A:
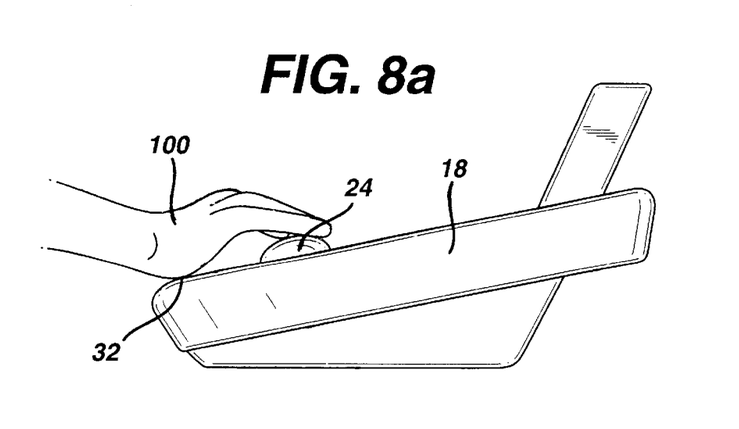

FIG. 8 illustrates a second embodiment of the present invention in which the wrist pad 32 of the keyboard is integrated into the front of the control panel 18 where it serves as a wrist pad for both the control panel and keyboard. The keyboard wrist pad 32 extends along the front of the control panel 18 and wraps up on top of the keyboard so as to provide a wrist pad for use when operating the trackball 24 and other controls on the control area 36, as shown in FIG. 8a. That drawing shows the hand 100 of a user manipulating the trackball 24 while resting the base of the hand on the wrist pad 32. Since the keyboard wrist pad serves as a wrist pad for the trackball and nearby controls of the control panel 18, it is not necessary that the molding 38 around the edge of the control panel be made of wrist pad material. The molding may if desired be make of a more durable rubberlike or polymeric material, preferably one with an appearance that matches that of the wrist pad 38 for a clean control panel appearance.

Figure 9:
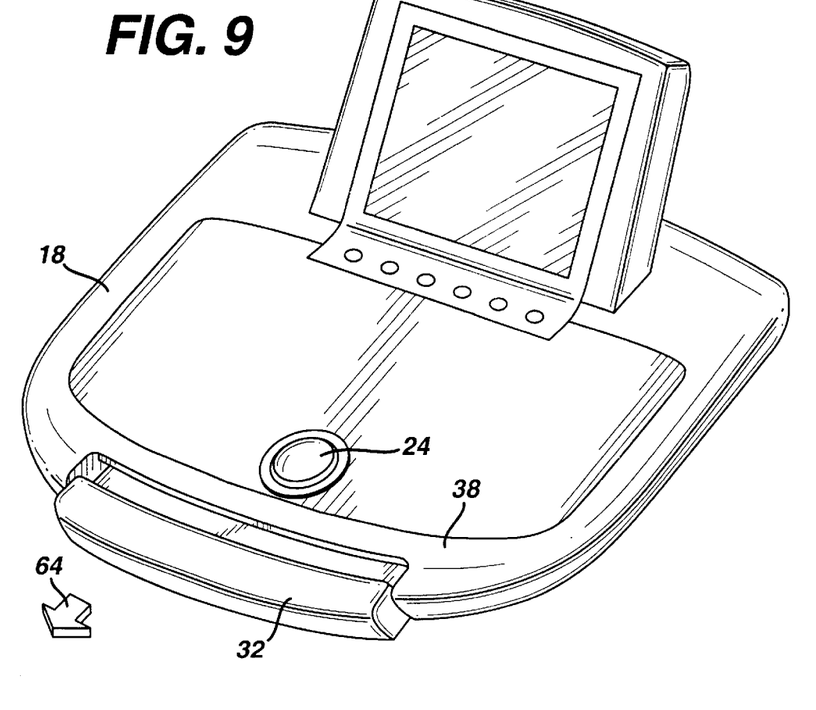
Figure 9A:
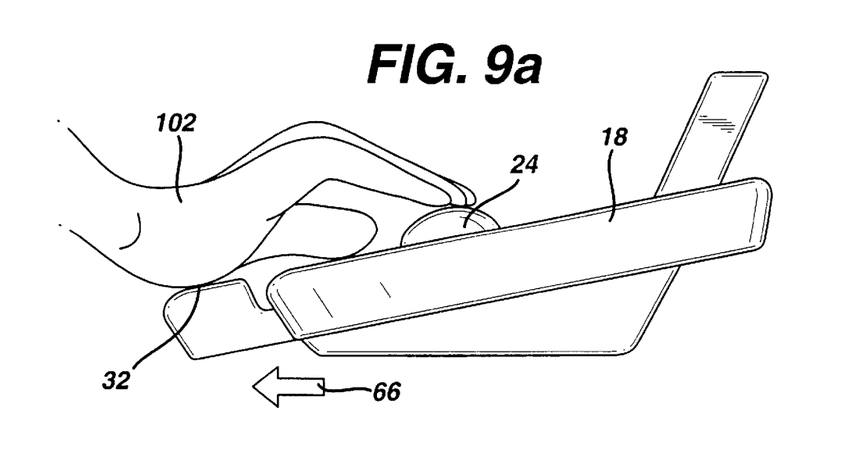

An additional benefit of using the keyboard wrist pad 32 to serve as the control panel wrist pad is that the movable keyboard allows the position of the wrist pad to be adjusted for different hand sizes. For instance, FIG. 9 shows the keyboard and its wrist pad 32 slightly extended from the recess in the front of the control panel 18, as indicated by the arrows 64,66. As FIG. 9a shows, in this extended position the wrist pad 32 can accommodate a larger hand 102 of a user. A compact control panel design can thus serve to provide wrist support for a wide variety of users.

Figure 10:
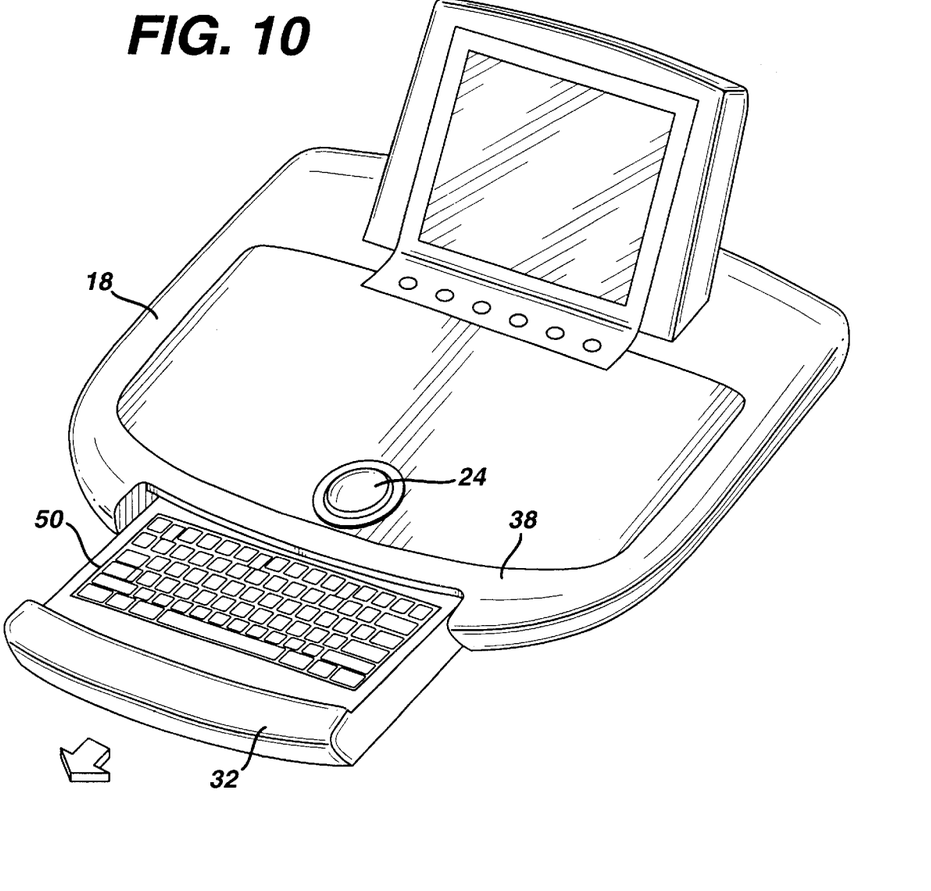

Finally, FIG. 10 illustrates the keyboard 50 and wrist pad 32 in a fully extended position, in which the user would be using the keyboard 50 while resting the wrist or base of the hand on the wrist pad 32.

Other variations will readily occur to those skilled in the art. For example, instead of or in addition to sliding straight out from the front of the control panel, the keyboard may be given other directions of movement. The keyboard can be mounted on a track or linkage similar to those described for the control panel in the concurrently filed U.S. patent application Ser. No. 10/155,459, which would enable the keyboard to move laterally from left to right with respect to the control panel. This articulation would enable the keyboard to be moved to one side of the control panel so that the user can be in close proximity to the control panel when the keyboard is extended. In FIG. 7, for instance, lateral articulation of the control panel 50 either linearly or along a curved path would enable the user to push the keyboard to one side and be able to sit close to the control panel while the keyboard is extended for use.

What is claimed is:

1. An ultrasonic diagnostic imaging system including a control panel by which the ultrasonic imaging system may be controlled, comprising:
   a control panel wrist pad located on the front of the control panel; and
   a keyboard having a wrist pad on the front of the keyboard, the keyboard being extendable from beneath the control panel, the keyboard wrist pad being integrated into the form of the control panel wrist pad.

2. The ultrasonic diagnostic imaging system of claim 1, wherein the control panel wrist pad conforms to the front and sides of the control panel.

3. The ultrasonic diagnostic imaging system of claim 1, wherein the control panel wrist pad has a top surface which supports a hand or wrist while operating a control panel control; the control panel also having a front surface recess from which the keyboard may be extended.

4. The ultrasonic diagnostic imaging system of claim 3, wherein the keyboard wrist pad has a front surface which integrates into the front surface of the control panel when the keyboard is retracted into the front surface recess of the control panel.

5. The ultrasonic diagnostic imaging system of claim 1, wherein the control panel and keyboard are movably mounted to swivel and articulate laterally.

6. The ultrasonic diagnostic imaging system of claim 5, further comprising a cart upon which the ultrasonic diagnostic imaging system is mounted,
   wherein the control panel and keyboard are movably mounted to swivel and articulate laterally with respect to the cart.

7. An ultrasonic diagnostic imaging system including a control panel by which the ultrasonic imaging system may be controlled, comprising:
   a keyboard movably mounted to retract or extend from beneath the control panel, the keyboard having a wrist pad which may support the hand or wrist of a user while operating a control on the control panel and the keyboard.

8. The ultrasonic diagnostic imaging system of claim 7, wherein the keyboard wrist pad retracts into or extends from the control panel as the keyboard is moved.

9. The ultrasonic diagnostic imaging system of claim 7, wherein the keyboard wrist pad has a top surface which serves as a wrist pad while operating a control on the control panel when the keyboard is in the retracted position, the keyboard wrist pad top surface serving as a wrist pad while operating the keyboard when the keyboard is in the extended position.

10. The ultrasonic diagnostic imaging system of claim 7, wherein the keyboard wrist pad has a top surface which serves as a wrist pad while operating a control on the control panel when the keyboard is in a partially retracted position, the keyboard wrist pad top surface serving as a wrist pad while operating the keyboard when the keyboard is in the extended position.

11. The ultrasonic diagnostic imaging system of claim 7, wherein the control panel includes a front edge into which the keyboard wrist pad integrates when the keyboard is in the retracted position.

12. The ultrasonic diagnostic imaging system of claim 11, wherein the control panel front edge is made of a rubberlike or polymeric material.

13. An ultrasonic diagnostic imaging system including a control panel by which the ultrasonic imaging system may be controlled, comprising:
   a control panel wrist pad located on the front of the control panel; and
   a keyboard having a wrist pad on the front of the keyboard, the keyboard being extendable from beneath the control panel, the keyboard wrist pad being integrated into the form of the edge of the control panel.

14. The ultrasonic diagnostic imaging system of claim 13, wherein the keyboard wrist pad is integrated into the form of the front edge of the control panel.

15. The ultrasonic diagnostic imaging system of claim 14, wherein the control panel front edge is made of a rubberlike or polymeric material.

16. The ultrasonic diagnostic imaging system of claim 13, wherein the keyboard wrist pad is integrated into the form of the top of the edge of the control panel.

17. The ultrasonic diagnostic imaging system of claim 16, wherein the control panel front edge is made of a rubberlike or polymeric material.

18. The ultrasonic diagnostic imaging system of claim 13, wherein the keyboard is mounted to extend laterally with respect to the control panel.

19. The ultrasonic diagnostic imaging system of claim 13, wherein the keyboard is also mounted to extend outward from the front of the control panel.

* * * * *